US006419670B1

United States Patent
Dikeman

(10) Patent No.: US 6,419,670 B1
(45) Date of Patent: Jul. 16, 2002

(54) GASTROSTOMY TUBE SET

(76) Inventor: W. Cary Dikeman, 12619 Pawnee La., Leawood, KS (US) 66209

( * ) Notice: Subject to any disclaimer, the term of this patent is extended or adjusted under 35 U.S.C. 154(b) by 0 days.

(21) Appl. No.: 09/505,381

(22) Filed: Feb. 16, 2000

(51) Int. Cl.[7] ............................................. A61M 25/16
(52) U.S. Cl. ...................................... 604/533; 604/910
(58) Field of Search ................................ 604/246, 249, 604/256, 523, 533, 535, 539, 537, 167.02, 905, 910, 167.03, 167.04; 251/149.1

(56) References Cited

U.S. PATENT DOCUMENTS

| | | | | |
|---|---|---|---|---|
| 3,645,562 A | * | 2/1972 | Fandetti | 285/73 |
| 4,076,285 A | * | 2/1978 | Martinez | 285/332 |
| 4,511,359 A | * | 4/1985 | Vaillancourt | 604/411 |
| 5,533,708 A | * | 7/1996 | Atkinson et al. | 251/149.1 |
| 5,833,275 A | * | 11/1998 | Anderson | 285/305 |

* cited by examiner

Primary Examiner—Michael J. Hayes
(74) Attorney, Agent, or Firm—Shughart Thomson & Kilroy

(57) ABSTRACT

A gastrostomy tube set includes a delivery tube assembly having a tube for placement in a stomach and a supply tube assembly. The delivery tube includes a valve assembly including an outwardly protruding housing presenting an infusion port and a circumferentially extending flange that protrudes radially outwardly. The supply tube has a distal end including a connector having a male element and a side wall with a lug protruding radially inwardly. The connector couples to valve assembly by orienting the connector with the lug displaced circumferentially from the flange, inserting the male element into the infusion port to shift the valve open, and rotating the connector about the longitudinal axis of the male element so that the lug engages the flange to prevent the connector from being pulled axially from the delivery tube assembly.

13 Claims, 2 Drawing Sheets

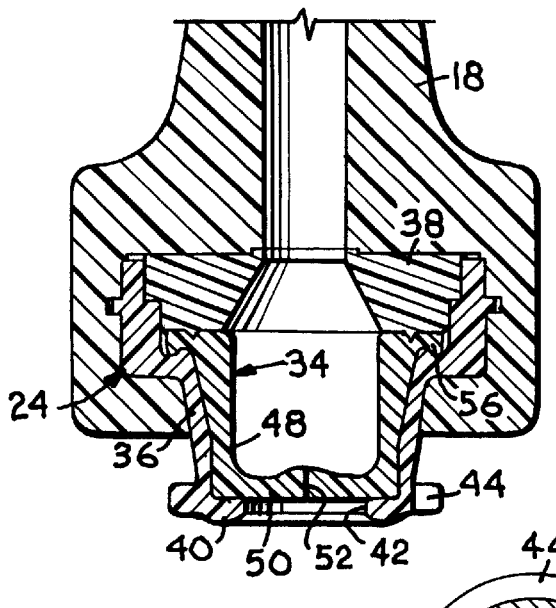
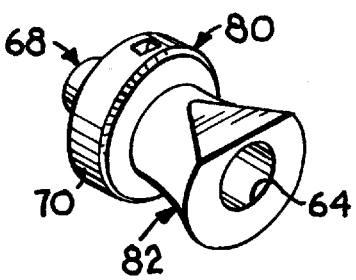
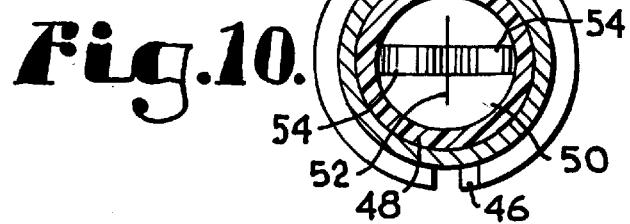
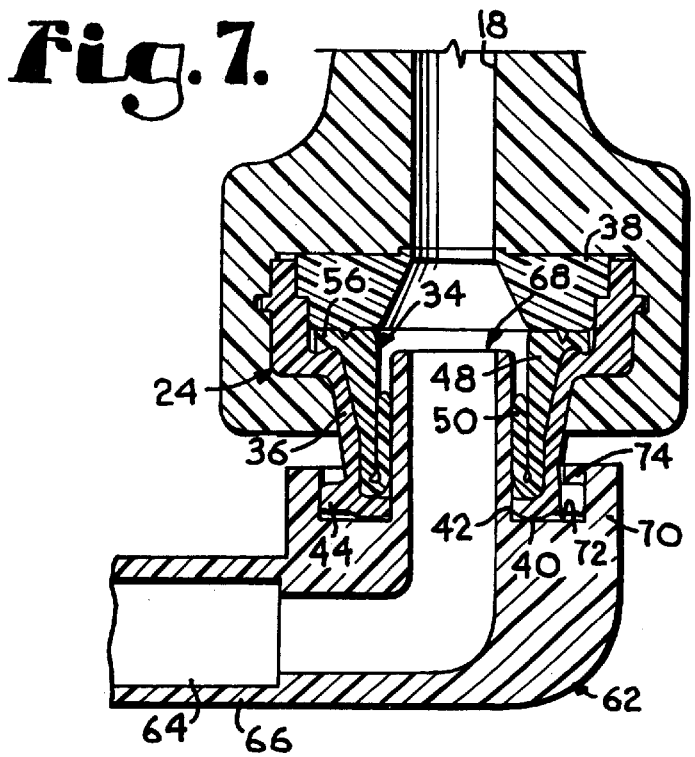
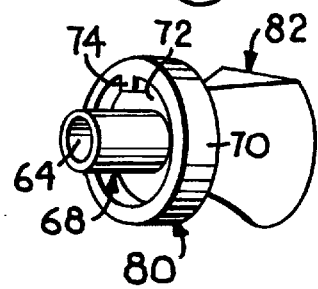

GASTROSTOMY TUBE SET

CROSS-REFERENCE TO RELATED APPLICATIONS

"Not Applicable".

STATEMENT REGARDING FEDERALLY SPONSORED RESEARCH OR DEVELOPMENT

"Not Applicable".

BACKGROUND OF THE INVENTION

The present invention relates generally to tube sets for use in supplying fluids such as food and medicine to the stomach of a human or other subject through a surgically constructed opening, and more particularly to a gastrostomy tube set having an improved coupling arrangement between a pair of tube assemblies of the set.

It is conventional to provide a gastrostomy tube set having a pair of tube assemblies, one of which is a delivery assembly adapted to remain in place in the stomach of a subject for an extended period of time, e.g. several months, and the other of which is a single-use supply assembly adapted to be coupled to the delivery assembly for a relatively short time, e.g. 12–24 hours. This known arrangement obviates the need for frequent replacement of the delivery assembly, while enabling the use of disposable, single-use supply assemblies for each infusion of nutrients and/or medicine into the stomach.

In a known tube set, the delivery tube assembly includes an elongated, flexible tube formed of silicone or the like and presenting a central fluid passage for permitting fluids to be introduced into the stomach of a subject. The tube also includes a relatively small-diameter second passage extending along a side of the fluid passage, and a sleeve of expandable material surrounds the tube adjacent the inner end thereof and is in communication with the second passage such that air can be introduced to the sleeve through the second passage to inflate the sleeve during placement of the delivery set. The outer end of the tube is formed into a hub or termination presenting an infusion port communicating with the central passage and an inflation port communicating with the second passage. A valve is disposed in each passage adjacent the port, and controls the introduction of fluids to the tube. In order to inflate the sleeve of the tube, the valve in the second passage is opened and air is forced into the second passage. Likewise, the valve in the central passage must be opened in order for nutrients or medicine to be supplied to the central passage.

The supply assembly of the known tube set includes a supply tube formed of silicone or the like and presenting a central fluid passage for permitting fluids to be supplied to the delivery tube assembly. In addition, the assembly includes a connector for permitting the assembly to be coupled with the delivery assembly and for shifting the valve in the central passage of the delivery tube to the open position. The connector is formed of a relatively rigid medical grade synthetic resin, and includes a male element sized for receipt in the infusion port of the delivery tube, and a radially protruding lug.

The infusion port of the delivery tube is circular, and includes a radially extending notch that is specially adapted to receive the lug of the connector. A circumferential groove extends around the inside of the central passage of the delivery tube just inboard of the infusion port, and communicates with the notch to receive the lug and enable the connector to be rotated about the longitudinal axis of the male element after the lug has been inserted into the notch, locking the connector in place on the termination of the delivery assembly. As such, the connector can only be inserted into the infusion port in a single orientation, and can then be rotated about the axis of the male element to lock the connector in place. Removal of the connector also requires that it first be rotated to a position in which the lug aligns with the notch before being withdrawn.

Although known gastrostomy tube set constructions perform their intended functions, numerous drawbacks and technical problems exist. For example, in the known constructions, the infusion valve is spaced from the infusion port by a distance of several millimeters, and the groove for receipt of the lug is inboard of the infusion port, creating a void or cavity within the central passage inboard of the port. This cavity is a collection point for fluids and bacteria, and is difficult to clean and disinfect. In addition, conventional infusion valve constructions do not provide a good seal against the male element of the connector during infusion, creating the possibility of leakage.

BRIEF SUMMARY OF THE INVENTION

It is an object of the present invention to solve the technical problems left unaddressed by the prior art, and to provide a gastrostomy tube set that is easy to use, easy to clean, presents a lower risk of infection than conventional constructions, and provides a better seal between the supply and delivery assemblies during infusion.

In accordance with these and other objects evident from the following description of a preferred embodiment of the invention, the gastrostomy tube set of the present invention includes a delivery assembly having a first tube adapted for placement in the stomach of the body and presenting an outer end, a termination connected to the outer end of the first tube and being adapted for placement against the external surface of the body, and a valve assembly disposed in the fluid passage of the termination and including a housing and a valve body disposed in the housing. The housing includes an elongated throat that protrudes from the termination and presents an infusion port communicating with the fluid passage, and at least one circumferentially extending flange that protrudes radially outward from the throat. The tube set also includes a supply tube assembly constructed of a second tube presenting a distal end to which a connector is secured. The connector includes an elongated tubular male element defining a longitudinal axis and being sized for receipt in the infusion port, and a side wall extending generally coaxially with the male element. The side wall presents a lug that protrudes radially inward toward the male element, and the connector is coupled to the valve assembly by orienting the connector with the lug displaced circumferentially from the flange, inserting the male element into the infusion port to shift the valve body to the second position, and rotating the connector about the longitudinal axis of the male element so that the lug engages the flange to prevent the connector from being pulled axially from the termination.

By providing a construction in accordance with the present invention, numerous advantages are realized. For example, by providing a valve assembly and connector in accordance with the present invention, it is possible to easily and securely couple the supply and delivery tubes of the set together. In addition, by providing an external flange on the housing of the valve assembly rather than an internal groove as is found in conventional constructions, the infusion port site is exposed for cleaning and disinfecting, and presents less risk of infection to the subject.

Preferably, the flange of the housing defines an outer diameter that is greater than 7.2 mm, which corresponds to the maximum diameter of the threaded locking collar of a conventional Luer fitting. As such, the delivery assembly of the tube set does not couple with a conventional Luer fitting, providing protection against the infusion of any fluids other than those specifically prescribed for introduction through the tube set into the stomach of the subject.

BRIEF DESCRIPTION OF THE SEVERAL VIEWS OF THE DRAWING

The preferred embodiment of the present invention is described in detail below with reference to the attached drawing, wherein:

FIG. 6 is a fragmentary sectional view of the delivery tube assembly, taken along line 6—6 of FIG. 3;

FIG. 7 is a fragmentary sectional view of the delivery tube assembly similar to FIG. 6, illustrating the connector of the supply tube assembly coupled with the delivery tube assembly of the tube set;

FIG. 8 is a top and front perspective view of an alternate connector adapted for use in the supply tube assembly;

FIG. 9 is a rear and side perspective view of the alternate connector; and

FIG. 10 is a sectional view taken along line 10—10 of FIG. 3.

DETAILED DESCRIPTION OF THE INVENTION

Figure 1:
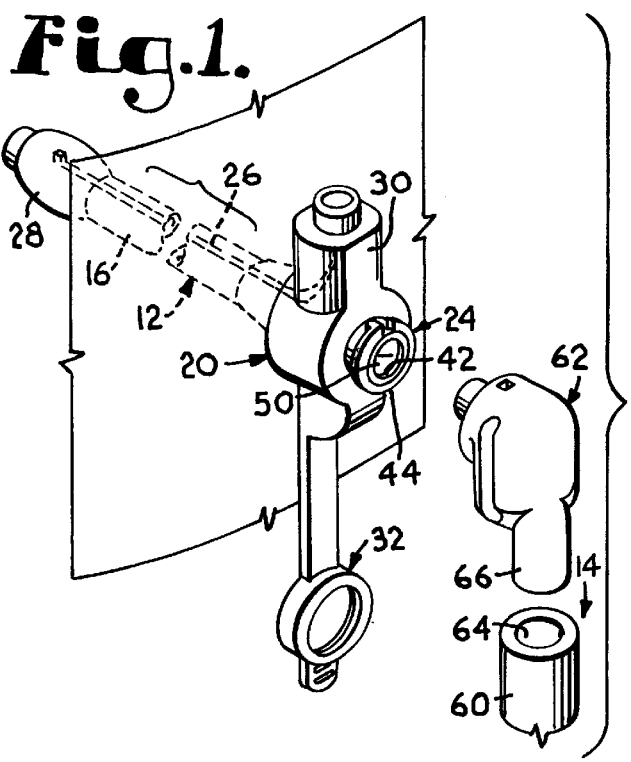
FIG. 1 is a fragmentary perspective view of a gastrostomy tube set constructed in accordance with the preferred embodiment of the invention, illustrating the tube set in a use position relative to a human body.

A gastrostomy tube set constructed in accordance with the preferred embodiment of the present invention is illustrated in FIG. 1, and broadly includes a delivery tube assembly 12 and a supply tube assembly 14. The delivery tube assembly 12 is adapted to be inserted into the stomach of a subject through an opening formed in an external surface thereof, and to remain in place over a treatment period of up to several months. The supply tube assembly 14 is adapted to be assembled on a conventional supply bag or the like to be filled with nutrients and/or medicine, and to be coupled to the delivery assembly for supplying such fluids to the stomach of the subject.

The delivery tube assembly 12 broadly includes a tube assembly including a tube 16 presenting inner and outer axial ends and a central fluid passage 18, a termination 20 formed in the outer end of the tube, and a pair of valve assemblies supported in the termination. The tube 16 and termination 20 are formed of any suitable medical grade material such as a silicone, and the tube is flexible and pliant to facilitate placement and use of the tube set.

The tube 16 includes an inner end opposite the termination, and the central fluid passage 18 extends completely through the tube for providing a flow path for fluids to be infused into the subject's stomach. A small second passage 26 is also formed in the tube and extends along substantially the entire length of the tube to a small,. radially extending outlet port that communicates with an expandable sleeve 28 that is adhered to the tube over the outlet port. The sleeve is inflated when pressurized air is introduced to the second passage. The sleeve 28 is constructed of a relatively thin tubular membrane of a medical grade synthetic resin material that is received over the end of the tube 16 and sealed at each end thereof to the tube. As such, when air is forced into the sealed space between the tube and the sleeve, the sleeve inflates, facilitating placement and securement of the delivery tube assembly in the subject.

The termination 20 is preferably formed as a part of the tube, but may alternately be formed separately and assembled on the outer end of the tube during construction. The termination includes a central hub presenting an enlarged outer diameter relative to the outer diameter presented by the tube, a radial protrusion 30 through which the second passage of the tube extends, and a cap 32 tethered to the hub. As shown in FIG. 6, the central passage of the tube passes through the hub of the termination and is stepped to define a cavity in which the infusion valve assembly 24 is received. The cavity includes a large diameter region that is spaced axially along the passage from the infusion port by a relatively small-diameter region. The large-diameter region is further provided with a circumferentially extending channel or groove that is adapted to retain the infusion valve assembly in place within the termination. The small-diameter region of the cavity presents an inner surface that is tapered along its length toward a small-diameter end defining an opening in the hub of the termination.

Returning to FIG. 1, the radial protrusion 30 of the termination includes a passage providing communication with the second passage 26 of the tube 16, and the passage presents an enlarged inner diameter relative to the second passage in order to receive the inflation valve assembly 22. A circumferentially extending channel or groove is formed in the passage and is adapted to retain the inflation valve assembly in place within the termination. The cap 32 protrudes from the hub of the termination in a direction diametrically opposed to the protrusion 30, and includes a generally cup-shaped cap and a tether connecting the cap to the hub. A small tab is also provided for facilitating handling of the cap.

The inflation valve assembly 22 is conventional, and forms no part of the present invention. The assembly generally includes a housing supported in the passage of the protrusion 30, and a valve body supported within the housing for movement between open and closed positions. The housing presents a side wall having a circumferentially extending ridge that is received in the channel of the passage, and functions to retain the housing in place. A conventional adhesive can also be used to secure the housing in place within the passage. The valve body permits air to be forced into the second passage to inflate the sleeve during placement of the delivery tube assembly, and can be closed subsequent to inflation to prevent air from being exhausted from the assembly.

As illustrated in FIG. 6, the infusion valve assembly 24 broadly includes a housing supported in the central passage of the hub, and a valve body 34 supported in the housing for movement between open and closed positions. The housing is formed of a suitable medical grade synthetic resin, and includes an outer element 36 and an inner element 38. The outer element 36 is generally cup-shaped, including a generally circular end wall 40 extending in a direction generally transverse to the axis defined by the central passage 18, and a generally cylindrical side wall that extends coaxially with the passage axis. The end wall 40 includes a central circular opening 42 defining the infusion port, and an annular rim extends around the port on the outside of the end wall for defining a seat against which the supply assembly seats when coupled to the delivery assembly.

The side wall of the outer element 36 is stepped to mate with the stepped inner cavity of the termination 20, and presents a cylindrical region having a circumferential ridge, and a tapered region extending between the cylindrical region and the end wall 40. The cylindrical region is sized for receipt in the large-diameter region of the termination cavity with the ridge received in the channel of the cavity to retain the housing in place. The tapered region of the housing extends along the tapered region of the termination cavity and protrudes axially from the hub a short distance, e.g. about 3 mm. The inner surface of the element 36 generally corresponds to the outer shape, except that the inner surface is stepped adjacent the open inner end of the element to define a seat for the inner housing element.

Figure 2:
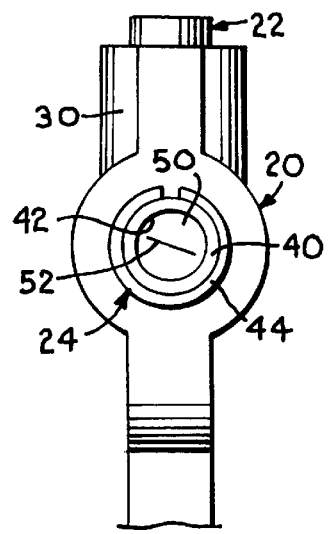
FIG. 2 is a fragmentary front elevational view of a delivery tube assembly forming a part of the tube set.
Figure 3:
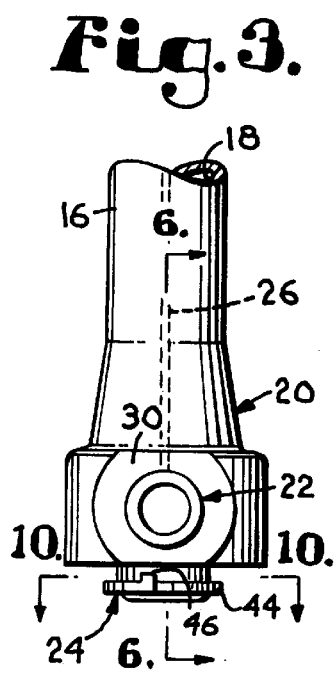
FIG. 3 is a fragmentary top plan view of the delivery tube assembly.

A circumferential flange 44 is provided on the tapered region of the outer element adjacent the end wall 40, and protrudes radially outward from the element to define an outer diameter larger than that of the throat of the element extending between the flange and the termination. With reference to FIG. 2, the flange 44 includes a pair of circumferential ends that are spaced from one another to define a gap sized for cooperation with the supply tube assembly to lock the two assemblies together during infusion, and one of the ends includes an axial protrusion 46 that extends along the throat toward the termination, as shown in FIG. 3.

Returning to FIG. 6, the inner housing element 38 is generally annular in shape, including a central passage extending coaxially with the central passage 18 and an outer circumferential surface sized for receipt in the inner end of the outer housing element 36. The outer circumferential surface of the inner element is stepped so that it seats against the stepped region of the outer element, and the two elements are preferably secured together during construction by ultrasonic welding, an adhesive or the like.

The valve body 34 is formed of a resilient medical grade elastomeric material, and is supported in the housing between the inner and outer elements. The body includes a tubular side wall 48 extending substantially parallel to the longitudinal axis and defining a first end and a second end, wherein the second end is in contact with the inner surface of the end wall. A thin flexible end wall or membrane 50 extends across the first end of the body. The membrane 50 includes a diametrical slit 52 that provides fluid communication through the membrane in the open position of the valve assembly.

The membrane 50 includes opposing surfaces, wherein the outer surface is substantially planar and the inner surface is preferably either planar or slightly convex. As shown in FIG. 10, a pair of ribs 54 are formed in the inner surface of the end wall and extend radially in a direction transverse to the length of the slit. The ribs 54 reinforce the membrane 50 and bias the slit 52 closed. In addition, the ribs support the membrane in the open position of the valve assembly.

As shown in FIG. 6, a circumferential flange 56 is provided at the first end on the valve body, and is sized for receipt between the inner and outer housing elements 38, 36. Preferably, the outer housing element 36 includes an annular ridge extending along the inner edge of the element between the large-diameter and small-diameter regions, and the inner element includes an annular ridge provided on the inner axial end face thereof. These annular ridges pinch the flange of the valve body to hold it in place during movement between the open and closed positions. In addition, the tapered region of the outer element presents a cylindrical inner surface adjacent the end wall 40 which is slightly smaller than the outer diameter of the side wall 48. Thus, the outer element firmly engages the body and applies a predetermined compression force for further biasing the material surrounding the slit 52 inwardly.

With reference to FIG. 1, the supply tube assembly 14 broadly includes a tube 60 having a first end adapted to be coupled with a bag or other receptacle in which fluids are stored, a second end secured to a connector 62, and a central fluid passage 64 extending between the ends in communication therewith. The tube 60 is formed of any suitable medical grade material such as a silicone, and is flexible and pliant to facilitate placement and use of the tube set.

Figure 5:
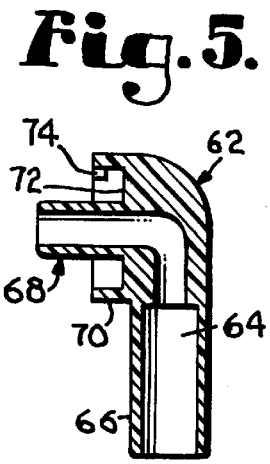
FIG. 5 is a sectional view of the connector, taken along line 5—5 of FIG. 4.

The connector 62 includes a first end 66 having a tubular configuration adapted for connection to the second end of the tube, and an opposite end having a construction adapted to mate with the housing of the valve assembly to lock the two assemblies together during infusion. As shown in FIG. 5, the second end of the connector extends at a 90° angle to the first end, creating an elbow connector shape, and includes an elongated tubular male element 68 that defines a longitudinal axis and is sized for receipt in the infusion port, a side wall 70 spaced radially from and extending generally coaxially with the male element, and an end wall 72 extending between the male element and the side wall in a plane generally transverse to the axis of the male element.

The male element 68 is tubular, presenting an inner passage that communicates with the central passage of the supply tube, and an outer cylindrical surface that engages the membrane of the valve body and shifts the membrane to an open position so that the inner passage of the connector communicates with the central passage of the delivery tube assembly, as shown in FIG. 7. Preferably, the outer diameter of the male element 68 is only slightly smaller than the diameter of the infusion port so that the end wall 40 of the housing supports the male element as it is inserted into the housing and engages the valve body.

The side wall 70 of the connector 62 faces inward toward the male element 68, and includes a diameter that is only slightly greater than the outer diameter defined by the flange 44 of the valve housing. As such, the end wall 40 and flange 44 of the valve housing are accommodated between the male element 68 and the side wall 70 of the connector when the male element is inserted into the infusion port. The end wall 72 limits the extent of insertion possible with the male element 68, and seats against the annular ridge on the end wall 40 of the valve housing to inhibit leakage between the elements during use.

Figure 4:
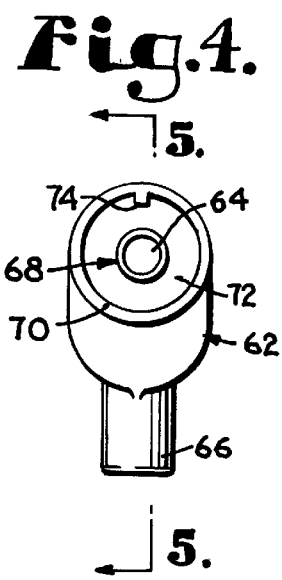
FIG. 4 is a rear elevational view of a connector of a supply tube assembly forming a part of the tube set.

As shown in FIG. 4, a lug 74 is provided on the side wall of the connector, and protrudes radially inward from the wall toward the male element. The lug 74 includes a circumferential width that is slightly smaller than the circumferential width of the gap defined between the ends of the flange of the valve housing, and is spaced radially from the axis of the male element by a distance greater than the diameter of the throat of the valve housing but less than the outer diameter of the flange. As such, in order to insert the male element 68 into the infusion port, the connector must first oriented with the lug aligned with the gap in the flange.

As shown in FIG. 5, the lug 74 is also constructed so that the distance between the end wall 72 and the axially inner end surface of the lug is greater than the axial distance between the end surface of the end wall 40 of the housing element and the axially inner end face presented by the flange 44. Thus, when the male element 68 is fully inserted into the infusion port until the end wall 72 of the connector seats against the end wall 40 of the housing, as shown in FIG. 7, the lug 74 moves completely through the gap in the flange 44, and the connector can be rotated to displace the lug circumferentially from the gap to lock the connector in place on the housing. Preferably, indicia are provided on the connector for facilitating proper orientation of the connector for coupling and uncoupling.

In this locked position, the membrane 50 of the valve body seals against the outer surface of the male element to prevent leakage, the end walls 40, 72 of the housing and connector seat against one another to further inhibit leakage, and the inner end face of the lug 74 engages the inner end face of the flange 44 to prevent the connector from being pulled from the housing. In addition, the connector 62 can be freely rotated between a plurality of rotational positions without releasing the connector for removal since the flange extends substantially the entire distance around the housing. Further, the axial protrusion 46 on the one circumferential end of the flange, shown in FIG. 3, prevents the connector from being rotated past it into alignment with the gap, providing a construction in which removal of the connector can only be accomplished by rotating the connector in a particular direction. This facilitates safe use of the tube set, and prevents inadvertent removal of the supply tube assembly during infusion.

With reference to FIG. 7, in order to remove the supply tube assembly 14 from its coupled position, the connector 62 is rotated to return the lug 74 into alignment with the gap, and the connector is pulled from the housing. The membrane 50 of the valve body releases the male element, and is returned to the sealed condition shown in FIG. 6, in which the slit 52 is closed and the end wall 50 bears against the end wall 40 of the housing. By providing this arrangement for the valve assembly, a relatively void-free construction results that is easy to clean and that presents a relatively small cavity or volume to be cleaned and disinfected. In addition, the arrangement provides improved sealing between the valve body and the male element of the connector.

One particular feature of the preferred embodiment includes constructing the valve housing so that it cannot be coupled with any type of supply source other than one with which the delivery set is intended for use. For example, by constructing the flange 44 with a diameter of greater than 7.2 mm, the housing prevents the delivery tube assembly from being coupled with a conventional Luer fitting. It is known that conventional Luer fittings include threaded collars that present minimum inner diameters ranging between about 7.0–7.2 mm. By constructing the flange of the valve housing with a diameter larger than the minimum diameters of such fittings, it is not possible to force such fittings into the valve assembly. Thus, medicines stored in bags or syringes having Luer fittings, which often are intended for intravenous use, cannot be coupled with the delivery tube assembly. This improves the safety of the tube set.

An alternate construction of a connector 80 is illustrated in FIGS. 8 and 9, wherein the fluid passage 64 through the connector is substantially straight rather than being turned as in the connector 62 shown in FIG. 5. In the alternate construction of FIG. 8, the connector 80 includes a first end 82 presenting an inlet port for connection to the second end of the tube, and a tapered outer surface that facilitates gripping of the end to couple the connector with the delivery tube assembly. A flattened surface can be formed in the first end for receipt of indicia or the like for indicating the proper orientation of the connector relative to the valve assembly of the delivery tube assembly to facilitate coupling and uncoupling. The second end of the connector includes a construction identical to the second end of the connector shown in FIG. 5, and is adapted to mate with the housing of the valve assembly to lock the two assemblies together during infusion.

As shown in FIG. 9, the second end of the connector 80 includes an elongated tubular male element 68 that defines a longitudinal axis and is sized for receipt in the infusion port, a side wall 70 spaced radially from and extending generally coaxially with the male element, and an end wall 72 extending between the male element and the side wall in a plane generally transverse to the axis of the male element. A lug 74 is provided on the side wall 70, and protrudes radially inward from the wall toward the male element. As such, use of the connector 80 is identical to use of the connector described above, the only difference being that the connector presents an elbow, and the connector is straight.

Although the present invention has been described with reference to the preferred embodiment illustrated in the attached drawing figures, it is noted that substitutions may be made and equivalents employed herein without departing from the scope of the invention.

What is claimed is:

1. A gastrostomy tube set for use in injecting fluids into the stomach of a body through an opening formed in an external surface of the body, the tube set comprising:

a first tube assembly including an inner end adapted for placement in the stomach of the body, an opposed outer end, and a fluid passage extending between the ends;

a valve assembly disposed in the fluid passage and including a housing and a valve body disposed in the housing, the valve body being movable between a first position blocking flow through the fluid passage and a second position permitting flow through the fluid passage, the housing protruding from the outer end of the tube assembly and presenting an infusion port communicating with the fluid passage, and at least one circumferentially extending flange that protrudes radially outward relative to the fluid passage;

a second tube adapted for placement outside the body and a connector secured to the distal end of the second tube and including an elongated tubular male element defining a longitudinal axis and being sized for receipt in the infusion port, and a side wall extending generally coaxially with the male element, the side wall presenting a lug that protrudes radially inward toward the male element, the connector being coupled to the valve assembly by orienting the connector with the lug displaced circumferentially from the flange, inserting the male element into the infusion port to shift the valve body to the second position, and rotating the connector about the longitudinal axis of the male element so that the lug engages the flange to prevent the connector from being pulled axially from the first tube assembly;

wherein the flange of the housing includes a pair of circumferential ends that are spaced from one another to define a gap sized for receipt of the lug of the connector when the male element is inserted into the infusion port; and wherein one of the ends of the flange includes an axial protrusion that prevents the lug from moving circumferentially past the one end in either direction.

2. The tube set as recited in claim 1, wherein the flange of the housing defines an outer diameter that is greater than 7.2 mm.

3. The tube set as recited in claim 1, wherein the flange of the housing defines an outer diameter and the side wall of the connector defines an inner diameter, the outer diameter of the flange being substantially equal to the inner diameter of the side wall.

4. The tube set as recited in claim 1, wherein the connector includes an end wall extending between the male element and the side wall, and said housing includes an end wall that engages the end wall of the connector when the male element is inserted into the infusion port of the housing to limit the extent to which the connector can be inserted.

5. The tube set as recited in claim 4, wherein, the flange of the housing includes an inner end surface in spaced relation to the outer end of said first tube assembly, and the axial spacing between the end wall of the connector and the lug is slightly greater than the axial distance between said housing end wall and the inner surface of the flange.

6. The tube set as recited in claim 1, wherein the connector includes indicia that indicate the location of the lug to facilitate orientation of the connector during coupling with the valve assembly.

7. The tube set as recited in claim 1, wherein the valve body is generally cup-shaped, including an end wall defining a slit, and a side wall supporting the end wall within the housing for movement between the first and second positions of the valve body.

8. A supply tube assembly for use in a gastrostomy tube set including a delivery tube assembly presenting an inner, stomach-engaging end, an opposed outer end, and a fluid passage therebetween, a valve assembly disposed in the fluid passage and including a housing and a valve body disposed in the housing, the valve body being movable between a first position blocking flow through the fluid passage and a second position permitting flow through the fluid passage, the housing protruding from the outer end of said delivery tube assembly and presenting an infusion port communicating with the fluid passage, and at least one circumferentially extending flange that protrudes radially outward relative to the fluid passage, the supply tube assembly comprising:

a supply tube presenting a distal end; and a connector secured to the distal end of the supply tube and including an elongated tubular male element defining a longitudinal axis and being sized for receipt in the infusion port, and a side wall extending generally coaxially with the male element, the side wall presenting a lug that protrudes radially inward toward the male element, the connector being adapted for coupling to the valve assembly by orienting the connector with the lug displaced circumferentially from the flange, inserting the male element into the infusion port to shift the valve body to the second position, and rotating the connector about the longitudinal axis of the male element so that the lug engages the flange to prevent the connector from being axially sybstsntially displaced from the delivery tube assembly while said connector is rotated relative to said housing.

9. The supply tube assembly as recited in claim 8, wherein the connector includes an end wall extending between the male element and the side wall that is adapted to engage the flange when the male element is inserted into the infusion port of the housing.

10. The supply tube assembly as recited in claim 8, wherein the connector includes indicia that indicate the location of the lug to facilitate orientation of the connector during coupling with the valve assembly.

11. A gastrostomy tube set for communicating a fluid with a stomach through a body opening and comprising:

an internal delivery tube including an inner end positioned within a stomach, an opposite outer end, and a fluid passage extending therebetween;

a housing connected to said delivery tube and including an infusion port having a port axis and communicating with said internal delivery tube, said housing having a flange extending radially and circumferentially at least partially about said port;

a valve member positioned within said infusion port and having an open con figuration to enable flow through said port and a closed configuration blocking flow through said port;

a connector member connected to a supply tube and separably engaged with said housing to communicate a fluid through said supply tube and said delivery tube;

said connector member including a tubular male element communicating with said supply tube and positioned to sealingly engage said valve member and to urge said valve member to said open configuration when engaged with said housing; and said connector member including a lug engageable with said flange of said housing to separably retain said connector member in engagement with said housing and to enable rotation without substantial axial displacement of said connector member about said port axis through a substantial rotational range relative to said housing.

12. The tube set as recited in claim 11, wherein the flange of said housing includes a pair of circumferential ends that are spaced from one another to define a gap sized for receipt of said lug when said connector member is engaged with said housing.

13. The tube set as recited in claim 12, wherein one of said ends of said flange includes an axial protrusion that prevents said lug from moving circumferentially past said one end in either direction.

* * * * *